United States Patent [19]

Segura et al.

[11] Patent Number: 4,590,938

[45] Date of Patent: May 27, 1986

[54] MEDICAL RETRIEVER DEVICE

[76] Inventors: Joseph W. Segura, 810 60th Ave. SW., Rochester, Minn. 55902; James F. Vance, Sr., R.R. 2 Box 10, Spencer, Ind. 47460

[21] Appl. No.: 607,219

[22] Filed: May 4, 1984

[51] Int. Cl.[4] ............................................. A61B 17/22
[52] U.S. Cl. .................................................... 128/328
[58] Field of Search ............... 128/328, 320, 304, 757, 128/307, 309, 311, 356

[56] References Cited

U.S. PATENT DOCUMENTS

| | | | |
|---|---|---|---|
| 651,395 | 6/1900 | Stapp | 128/304 |
| 654,763 | 7/1900 | Russell | 128/304 |
| 1,612,697 | 12/1926 | Cecil | |
| 1,677,671 | 7/1928 | Councill | |
| 2,918,919 | 12/1959 | Wallace | 128/328 |
| 2,943,626 | 7/1960 | Dormia | 128/328 |
| 3,008,467 | 11/1961 | Morris | 128/328 |
| 3,074,408 | 1/1963 | Chester | 128/328 |
| 3,108,593 | 10/1963 | Glassman | 128/328 |
| 3,181,533 | 5/1965 | Heath | 128/320 |
| 3,739,784 | 6/1973 | Itoh | 128/320 |
| 3,791,387 | 2/1974 | Itoh | 128/320 |
| 3,805,791 | 4/1974 | Seuberth et al. | 128/304 X |
| 4,046,150 | 9/1977 | Schwartz et al. | 128/328 |
| 4,347,846 | 9/1982 | Dormia | 128/328 |

OTHER PUBLICATIONS

Joseph W. Segura, M.D., et al., "Percutaneous Removal of Kidney Stones, Preliminary Report," *Mayo Clinic Proceedings* (1982; 57:615-619).

Commercial Literature re Polypectomy Snares, American Endoscopy, Inc.

"Bard Announces ... A New Degree of Tactile Sensitivity in a Single Use, Disposable Ureter of Stone Extracter," Bard Urological Division C. R. Bard, Inc., Murray Hill, NJ, Copyright 1982, 4 pages.

"Stone Removers", American Cytoscope Makers Incorporated, New York, NY.

"Miscellaneous Urological and Other Specialties," B17-B18.

*Primary Examiner*—Michael H. Thaler

[57] ABSTRACT

An improved medical retriever device sized and adapted for use through the working channel of an endoscope for removing stones and the like from the kidneys, ureter or biliary duct. The device is of the type having an elongated, narrow sheath, a basket of relatively large diameter extendible from the distal end of the sheath and collapsible when withdrawn into the sheath, and remote means to project, retract and rotate the basket relative to the distal end of the sheath. The basket is defined by a multiplicity of spaced apart, outwardly bowed spring strips which extend generally axially of the sheath and are joined at respective distal and proximal ends of the basket. The strips are generally flat, with a ratio of radial to circumferential dimensions of between about 1:2 and 1:4, at least two of the strips at the distal extremity of the basket being disposed face to face and joined together in a manner contributing stiffness to the end of the basket. The basket shown has a generally bulbous form at its distal end, which is relatively stiff due to the spring strip construction and facilitates the dislodgement and capture of stones.

6 Claims, 17 Drawing Figures

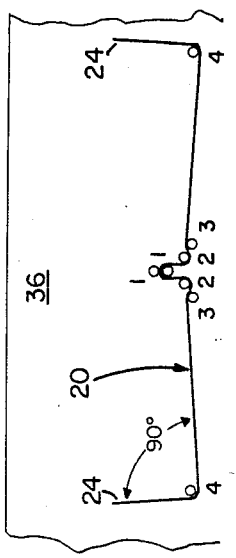
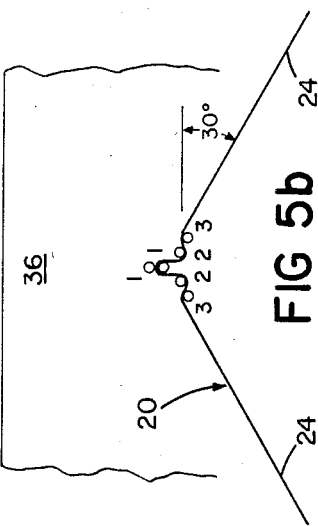
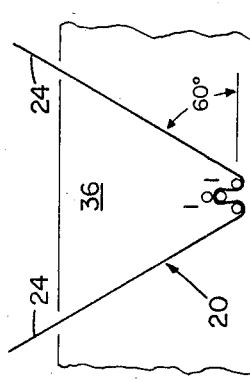
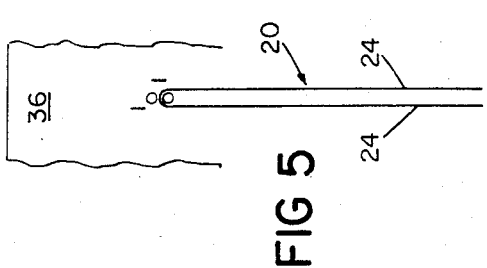
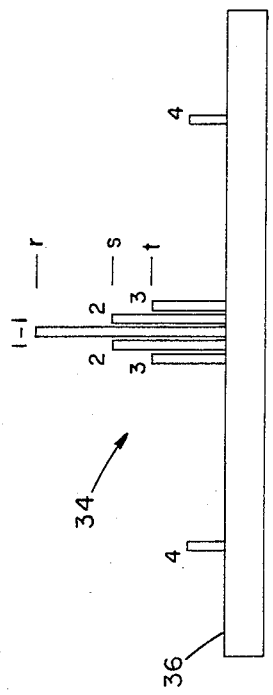
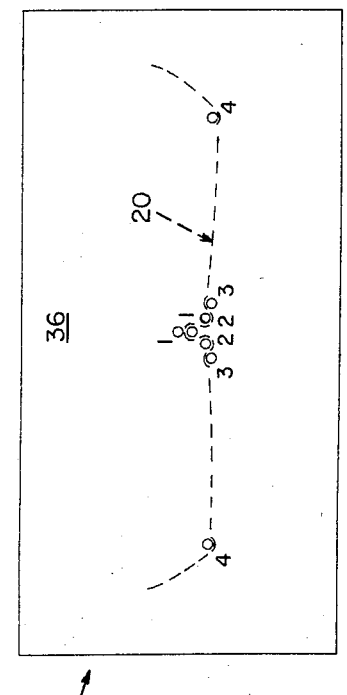
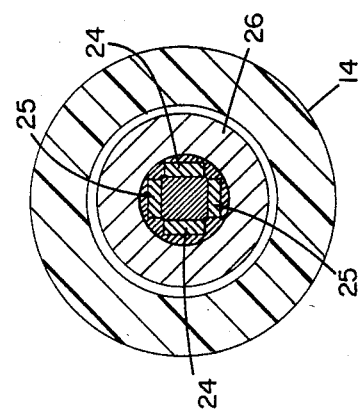
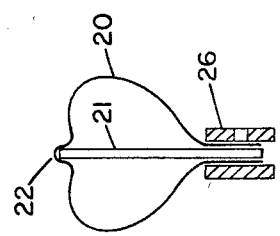

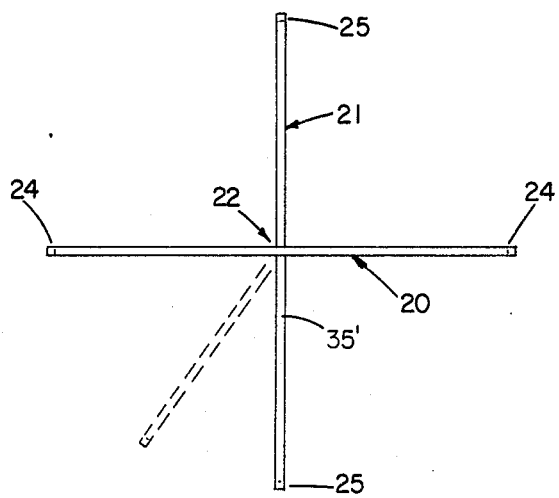
FIG 7a
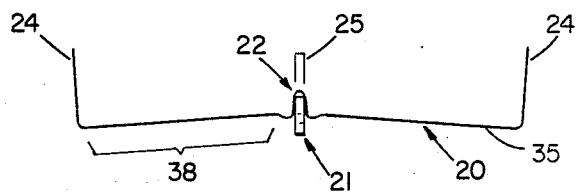
FIG 7
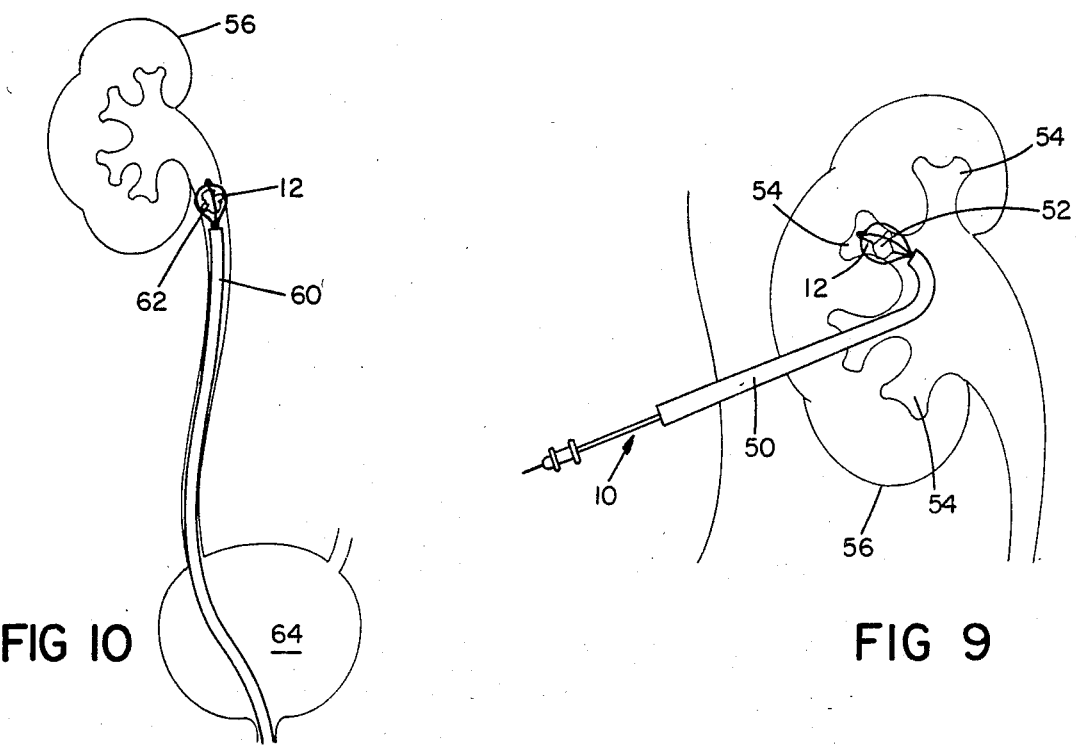
FIG 10
FIG 9

MEDICAL RETRIEVER DEVICE

BACKGROUND OF THE INVENTION

This invention relates to medical devices for removing stones from the kidneys, ureter or biliary duct.

While stones can be removed by direct surgery, it is much preferred that the stone be located by use of an endoscope and removed by endoscopic guidance of a device inserted through a working channel of the endoscope. Examples of instruments used in the past for removal of stones include forceps with axially-directed grasping arms, and basket devices such as shown in Councill U.S. Pat. No. 1,677,671, and baskets with helically arranged wires as shown in Dormia U.S. Pat. No. 2,943,626 and U.S. Pat. No. 4,347,846, e.g. similar to those sold by C. R. Bard, Inc. of Murray Hill, New Jersey.

It is an object of this invention to provide a device that can dislodge and remove stones more effectively than prior devices.

SUMMARY OF THE INVENTION

The invention applies to devices of the type sized and adapted for use through the working channel of an endoscope comprised of an elongated, narrow sheath, a basket of relatively large diameter extendible from the distal end of the sheath and collapsible when withdrawn into the sheath, the basket defined by a multiplicity of spaced apart, outwardly bowed spring arms which extend generally axially of the sheath and are joined at respective distal and proximal ends of the basket, and remote means to project, retract and rotate the basket relative to the distal end of the sheath.

According to one aspect of the invention, the basket is defined by a set of at least three generally flat strips, the ratio of radial to circumferential dimensions of the strips being between about 1:2 and 1:4, at least two of the strips at the distal extremity of the basket being disposed face to face and joined together in a manner contributing stiffness to the end of the basket. According to another aspect of the invention, the basket has a generally bulbous form adjacent its distal end, and in preferred embodiments the basket is comprised of at least four spring strips joined at the distal tip of the basket.

In preferred embodiments of the invention, at least one pair of the spring strips forming the basket is comprised of a single length of material formed into a loop; the ratio of radial to circumferential dimension of the strips is about 1:3, preferably the radial dimension being about 0.005 inch and the circumferential dimension about 0.015 inch; the proximal ends of the generally flat spring strip are joined within a sleeve which itself is retractable into the sheath; and a first portion of the generally flat strip closely adjacent the distal extremity of the basket lies at an acute angle of the order of about 15 degrees to the axis of the basket in a manner to facilitate collapse of the basket during withdrawal into the sheath, and a second contiguous outwardly curved portion of the strip leads to an outward shoulder of maximum basket diameter, the point of maximum diamter being spaced from the distal tip between about one quarter and one third the overall length of the basket.

PREFERRED EMBODIMENT

We first briefly describe the drawings:

DRAWINGS

FIG. 2 is an enlarged side sectional view of the distal portion of the device of FIG. 1 with the basket extended, while

FIGS. 4 and 4a are side and plan views of a forming device used to shape the spring arms;

FIG. 5 through 5c are sequential diagrammatic views of the preferred forming process;

FIG. 6 is an enlarged plan view of a strip in position on the forming device of FIG. 4, while

FIGS. 7 and 7a are side and plan views, respectively, of the step of joining the strip at the distal tip;

FIG. 8 is a side view of the strips with their proximal ends inserted into a sleeve, while FIG. 8a is an enlarged end section view at the lines 8a—8a of FIG. 3;

FIG. 9 is a diagrammatic view of the device inserted into the kidney via a nephroscope; and FIG. 10 is a view similar to FIG. 9 of the device inserted into the ureter via a ureterscope.

STRUCTURE

Figure 1:
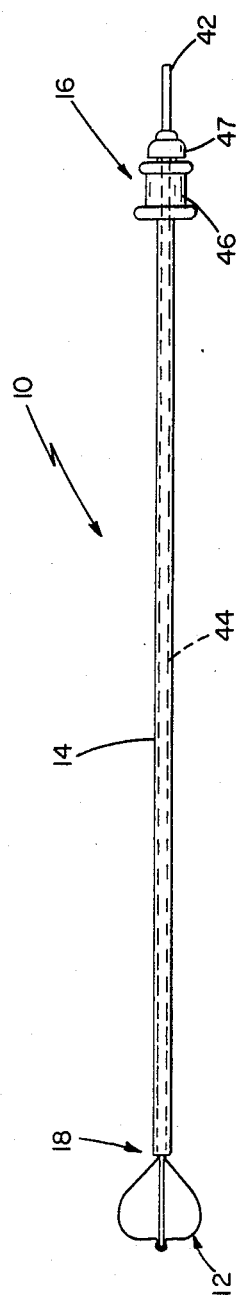
FIG. 1 is a diagrammatic view of one embodiment of a device according to the invention.

Referring to FIG. 1, a preferred medical retriever device 10 according to the invention consists of a distally bulbous basket 12, a narrow, elongated sheath 14 and a handle 16 at the proximal end. The sheath is a plastic tube, e.g. PVC or teflon, about 70 cm in length and sized for passage through the working channel of an endoscope. The sheath is 5 French (0.065 inch outer diameter), with an internal diameter of 0.044 inch.

Figure 2:
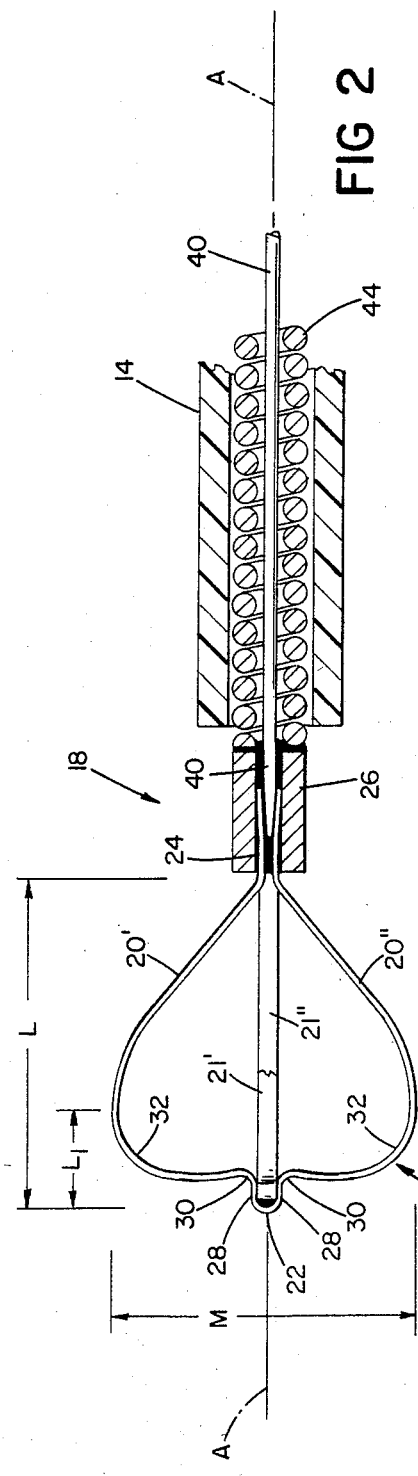

In FIG. 2, the distal portion 18 of the device is shown in more detail. Basket 12 comprises four outwardly bowed, generally flat spring arms 20', 20", 21', 21", opposed pairs of arms being formed each of a single length of strip-form 20, 21 material formed into a loop at distal tip 22, with the ends 24, 25 disposed in sleeve 26 at the proximal end of the basket. The strip-form arms, each about 3.0 inches in length, are typically of 304 stainless steel. The strips have their narrow dimension (x dimension) disposed radially and their broad dimension (y dimension) disposed circumferentially about the basket. In the embodiment shown, the strips are 0.005 inch by 0.015 inch in x and y dimension, respectively. Adjacent distal tip 22, first strip portions 28 lie at small acute angles to the axis, A, of the basket in a manner to facilitate collapse of the basket when it is retracted into the sheath, as will be described more fully below. Proximally and outwardly from portions 28, the spring strips have a curve shape consisting of a first outwardly directed (concave) arc 30 followed by a second, more proximal, inwardly directed (convex) arc 32, the centers of the arcs, e, f, respectively, being separated by about 0.035 inch. The maximum diameter, M, of the basket is reached at a position spaced dimension $L_1$ from the distal tip. In the preferred embodiment, M equals about 1.7 cm, the length of the basket, L, is about 2.6 cm, and $L_1$ equals about 174 L.

Figure 6:
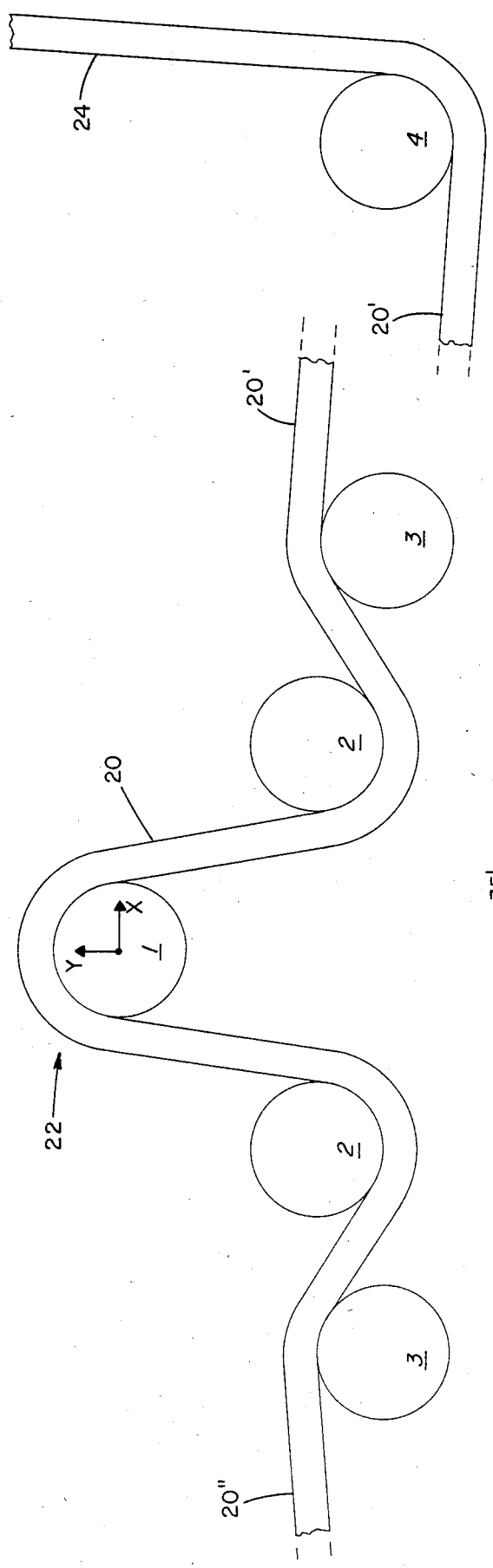

Referring to FIG. 5 et seq., the basket spring strips are formed in their novel configuration on the pin fixture 34 shown in FIGS. 4 and 4a. Referring to FIGS. 4a and 6, with the intersection of the X and Y axes, i.e. point (0, 0), at the center point of lower pin 1, the center points of the other pins in fixture 34 are disposed as follows (all dimensions are in inches): pins 2—2 at (0.030, −0.030) and (−0.030, −0.030); pins 3—3 at (0.060, −0.040) and (−0.060, −0.040); and pins 4—4 at (1.060, −0.040) and (−1.060, −0.040). All pins have diameter of about 0.020 inch.

A first length of spring strip material 20 is centered between pins 1—1 and the ends of the strip are bent parallel (FIG. 5) to form a small radius curve without kinking. As shown in FIG. 4, outward sets of pins are progressively shorter to allow strip 20 to be moved toward the base 36 after each step to engage further sets of pins for the next steps. Thus during the step just described, the strip is positioned on pins 1—1 at a height between r and s; for the next step, the strip is moved toward the base between s and t, to allow engagement about pins 2—2. Strip ends 24 are bent upward to approximately a 60° angle (FIG. 5a). The strip is again moved toward the base, and the ends 24 are bent about pins 3—3 to an angle of approximately minus 30° (FIG. 5b). The distance between the center of the arcs formed about pins 2 and 3 control the shape of the curve described above. For the embodiment described, this distance is about 0.035 inch. As the strips are bent in the direction of their thickness, the curves generally conform closely to the pin circumferences. The strip is again moved toward the base and the ends 24 are bent about pins 4 to an angle of about 90° (FIG. 5c). In FIG. 6, the strip is shown in enlarged scale formed about the pins.

Referring to FIGS. 7 and 7a, two strips 20, 21 formed as above are disposed at right angles, with the center protrusions formed on pins 1—1 in alignment. The undersurface 35 of strip 20 is disposed in close, flat-surface-to-flat-surface juxtaposition with the upper surface 35' of the strip 21. The strips are then joined securely, e.g. by silver soldering, to form tip 22, of minimal length, e.g., as compared to the length of the basket.

The undersurfaces 35 of portions 38 of the ends of the strip lying between the curves formed about pins 3 and 4 is rolled over a 0.25 inch diameter dowel to work harden the material into a permanent bow.

The arms of the strip are bent downward to bring the opposed ends 24, 25 of the strips 20, 21 into face-to-face contact and the ends are inserted into sleeve 26, 19.5 gauge stainless steel about 1 cm in length, and silver soldered. As shown in FIG. 8a, the springiness of the strips urges the ends radially outward against the walls of the sleeve 26 to form a uniform square pattern within.

Figure 6A:
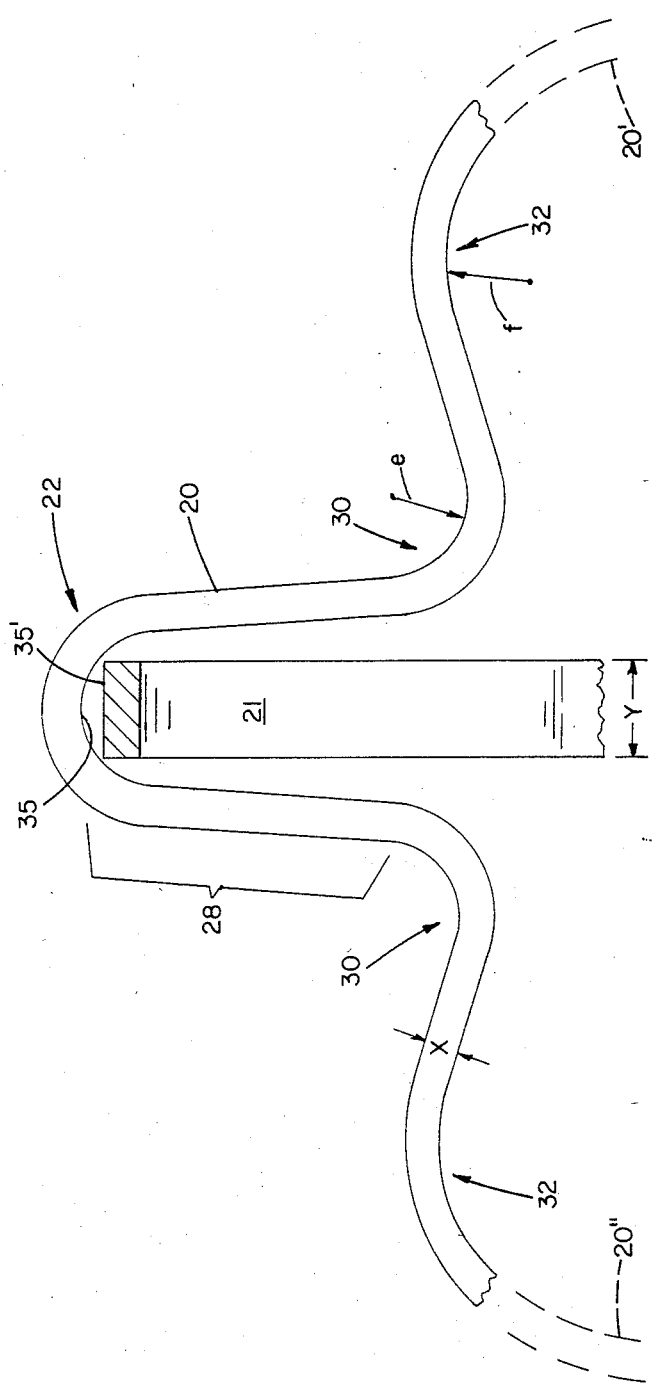
FIG. 6a is a similar viw of the strip used in the described device, with a second pair of arms in section.

Referring to FIG. 6a, the arms deform about the distal tip 22 with arcs 30, 32 flattening slightly to form an outwardly extending shoulder while the width of the proximal end of the tip narrows slightly.

Due to the special curved formation of the spring arms, the diameter of the basket 12 increases quickly from the distal end 22 of the basket giving the basket its novel, distally bulbous shape, the usefulness of which in dislodging and capturing stones and the like will be described more fully below. In the preferred embodiment, no such curves are formed at the proximal end of the basket, thus the diameter change occurs more gradually in this region.

After the proximal ends of the spring strips 20, 21 are secured, the distal end of shaft 40, 0.012 inch diameter stainless steel, is secured within sleeve 26. Surrounding shaft 40 and extending over the major portion of its length is stainless steel coil 44, about 0.038 inch diameter. Secured to the proximal end of shaft 40 is handle sleeve 42, 19.5 gauge stainless steel about 12 cm long. The ends of the shaft are typically secured by soldering, which is performed in a manner to fix the ends of the coil at least close to the ends of the sleeves. The shaft provides stiffness and torque, the coil provides flexibility and strength. Positionable on handle sleeve 42 is pin vise handle 46 provided to facilitate projection, retraction and rotation of basket 12 by movement of sheath 14 relative to the coil and shaft.

OPERATION

Figure 3:
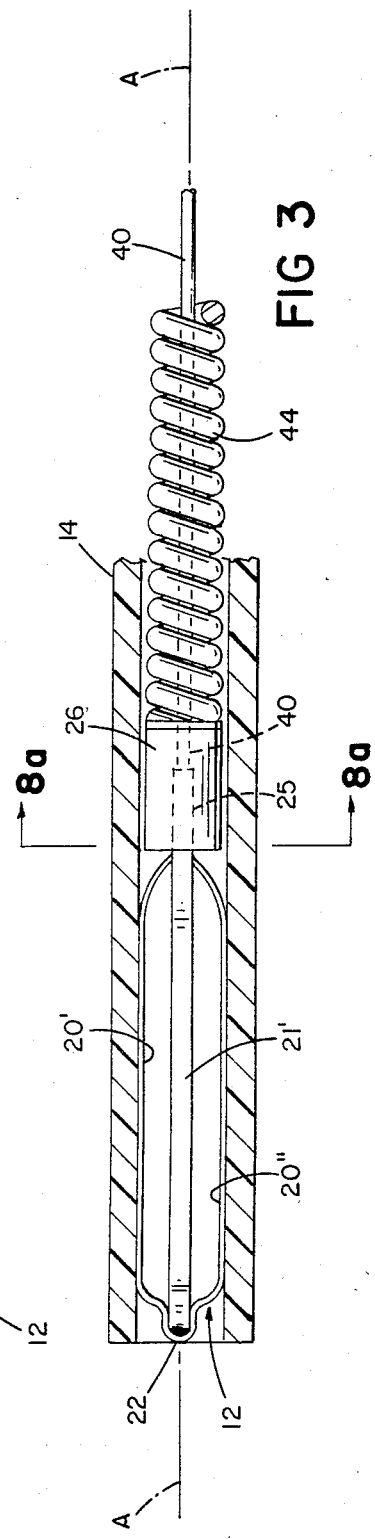
FIG. 3 is a similar view with the basket retracted.

Referring to FIGS. 1 and 3, sheath 14 is advanced distally to retract basket 12 into the sheath. As the sheath advances, the basket narrows and lengthens. When the basket is fully retracted, the pin vise 47 on handle 46 is tightened to secure the basket in retracted position. (In the embodiment shown in FIG. 3, the basket may be drawn fully into the sheath; in other embodiments, the distal tip 22 is of a size to act as a stop against the tip of the sheath to limit retraction.)

The surgeon positions the viewing lens of an endoscope within the body of a patient and by manipulating the scope, he visually locates a stone or the like to be removed. For example, the kidney is like a sponge with a central cavity the size of a walnut surrounded by spongy walls with numerous shallow crevices, or calyces, within which the stones typically lodge. In FIG. 9, the surgeon has positioned a nephroscope 50 with the tip positioned to view a stone 52 lodged in calyces 54 of the kidney 56. The device 10 with the basket retracted is inserted through the working channel of the scope. The surgeon extends the basket 12 from the sheath and the strip-form arms spring outward to restore the basket to the desired bulbous shape. As the surgeon manipulates the basket under visual guidance of the scope by rotating the handle and moving it in and out to try to dislodge the stone and move it into the volume of the basket, the relatively broad, flat surfaces of the spring strips act to deflect the spongy kidney tissue surrounding the stone while the distally enlarged volume of the basket close to the distal tip allows the surgeon to act with more effect to dislodge and capture the stone. It has been observed that the generally flat, tissue-deflecting surfaces of the spring strips of the device described; the extended dimension of the strip lying in the circumferential direction, which adds stiffness in that direction; the relatively stiff structure formed by the face-to-face disposed strips at the distal end, the adjacent strips acting as braces during engagement for dislodging; as well as the enlarged, bulbous distal shape of the basket, all serve to make this device highly effective for dislodging and removing stones and the like.

Once the stone is manipulated into the basket through the openings between the strips, the basket is partially retracted into the sheath to close the basket about the stone and hold it securely. Depending upon the size of the stone, and the likelihood of finding other stones to be removed, the sheath and the stone are either withdrawn through the endoscope, or the entire scope is removed.

OTHER EMBODIMENTS

Other embodiments are within the following claims. For example, a different number of strip-form arms may be employed, with consideration being given, for the particular application, for the open space required for entry of the stones into the volume of the basket. Where an odd number of arms is desired, the distal end of the odd arm is secured at the top, as shown in dashed line in FIG. 7a. Within certain broad aspects of the invention, the basket may be comprised of a number of single arms, the basket may be formed without a bulbous shape, or the curves may be provided at both ends of the basket.

Baskets of other sizes may be formed. For example, for the uses described above, the maximum basket diameter, M, may range between 1.2 and 2.2 cm, the basket length, L, may range between 2.2 and 3.0 cm, and $L_1$ may vary between $\frac{1}{4}$ L and about $\frac{1}{3}$L.

The device in these and other sizes is also useful with other endoscopes for retrieval of stones or the like from other parts of the body. For example, in FIG. 10 the retriever device 10 is shown in use via the working channel of a ureterscope 60 to remove a stone from the upper ureter. (The scope has been inserted, without an incision, via the bladder 64.) Once a stone 62 is observed, the surgeon extends the tip of the sheath, with the basket retracted, beyond the stone and then withdraws the sheath to allow the basket to expand. The generally flat-surface of the expanded arms aids in dilating the passage walls to help dislodge the stone and allow it to enter the basket for removal.

What is claimed is:

1. In a medical retriever device sized and adapted for use through the working channel of an endoscope for removing stones and the like from the kidneys, ureter or biliary duct, said device comprising an elongated, narrow sheath, a basket of relatively large diameter extendible from the distal end of said sheath and collapsible when withdrawn into said sheath, said basket defined by a multiplicity of spaced apart, outwardly bowed spring arms which extend generally axially of said sheath and are joined at respective distal and proximal ends of said basket, and remote means to project, retract and rotate said basket relative to the distal end of said sheath, the improvement wherein said basket has a generally bulbous form adjacent its distal end, the maximum diameter of said basket being spaced from the end of said basket a distance of equal to between about one quarter and one third the overall length of said basket.

said bulbous form defined by a set of generally flat spring strips, first portions of said generally flat spring strips closely adjacent the distal extremity of said basket lying at an angle close to the axis of said basket in a manner to facilitate collapse of said basket during withdrawal into said sheath, and second portions of said strips proximal of said first strip portions extending outwardly of the first strip portions, and having a curved shape comprised sequentially of oppositely directed arcs, the ratio of radial to circumferential dimensions of the material of said strips of said basket being between about 1:2 and 1:4, at least two of said strips at the distal extremity of said basket being disposed face to face and joined together in a manner contributing stiffness to said bulbous end of said basket.

2. The medical retriever device of claim 1 wherein said basket is comprised of at least four of said spring strips joined at the distal tip of said basket.

3. The medical retriever device of claim 1 wherein at least one pair of said spring strips forming said basket is comprised of a single length of strip-form material formed into a loop.

4. The medical retriever device of claim 1 wherein said ratio is about 1.3.

5. The medical retriever device of claim 4 wherein said strip has a radial dimension of about 0.005 inch and a circumferential dimension of about 0.015 inch.

6. The medical retriever device of claim 1 wherein the proximal ends of said generally flat spring strip are joined within a sleeve retractable into said sheath.

* * * * *

UNITED STATES PATENT AND TRADEMARK OFFICE
CERTIFICATE OF CORRECTION

PATENT NO. : 4,590,938

DATED : May 27, 1986

INVENTOR(S) : Joseph W. Segura and James F. Vance, Sr.

It is certified that error appears in the above-identified patent and that said Letters Patent are hereby corrected as shown below:

Col. 2, line 65, "174L" should be --1/4L --.

Col. 6, line 4, "distal" should be inserted before "end".

Signed and Sealed this

Twenty-sixth Day of August 1986

[SEAL]

Attest:

DONALD J. QUIGG

Attesting Officer

Commissioner of Patents and Trademarks